(12) United States Patent
Ko et al.

(10) Patent No.: US 10,870,621 B2
(45) Date of Patent: Dec. 22, 2020

(54) METHOD FOR PREPARING LATANOPROSTENE BUNOD, AND INTERMEDIATE THEREFOR

(71) Applicant: YONSUNG FINE CHEMICAL CO., LTD., Hwaseong-si (KR)

(72) Inventors: Eun Jeong Ko, Bucheon-si (KR); Hyun Ik Shin, Suwon-si (KR); Kee Young Lee, Seoul (KR); Chang Young Oh, Seongnam-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/636,955

(22) PCT Filed: Aug. 3, 2018

(86) PCT No.: PCT/KR2018/008854
§ 371 (c)(1),
(2) Date: Feb. 6, 2020

(87) PCT Pub. No.: WO2019/031774
PCT Pub. Date: Feb. 14, 2019

(65) Prior Publication Data
US 2020/0165199 A1    May 28, 2020

(30) Foreign Application Priority Data

Aug. 9, 2017 (KR) .......................... 10-2017-0101252

(51) Int. Cl.
*C07C 405/00* (2006.01)
*C07C 201/02* (2006.01)
*C07C 203/02* (2006.01)

(52) U.S. Cl.
CPC .................................. *C07C 405/00* (2013.01)

(58) Field of Classification Search
USPC ........................................................ 560/121
See application file for complete search history.

(56) References Cited

U.S. PATENT DOCUMENTS 7,273,946 B2    9/2007  Ongini et al.

FOREIGN PATENT DOCUMENTS

| KR | 10-0637296 B1 | 10/2006 |
| KR | 10-2006-0113753 A | 11/2006 |
| KR | 10-2013-0093093 A | 8/2013 |
| WO | 2017/093771 A1 | 6/2017 |

OTHER PUBLICATIONS

Weixia Li et al., "Biological activity evaluation and structure-activity relationships analysis of ferulic acid and caffeic acid derivatives for anticancer", Bioorganic & Medicinal Chemistry Letters, 2012, pp. 6085-6088, vol. 22.
International Search Report for PCT/KR2018/008854 dated Nov. 15, 2018 [PCT/ISA/210].

*Primary Examiner* — Ana Z Muresan
(74) *Attorney, Agent, or Firm* — Sughrue Mion, PLLC

(57) ABSTRACT

The present invention relates to a process for preparing latanoprostene bunod and an intermediate therefor. In accordance with the preparation process of the present invention, latanoprostene bunod can be efficiently and cost-effectively prepared while reducing side reactions.

8 Claims, No Drawings

METHOD FOR PREPARING LATANOPROSTENE BUNOD, AND INTERMEDIATE THEREFOR

CROSS REFERENCE TO RELATED APPLICATIONS

This application is a National Stage of International Application No. PCT/KR2018/008854 filed Aug. 3, 2018, claiming priority based on Korean Patent Application No. 10-2017-0101252 filed Aug. 9, 2017.

TECHNICAL FIELD

The present invention relates to a process for preparing latanoprostene bunod and an intermediate therefor. More particularly, the present invention relates to a cost-effective and efficient process for preparing latanoprostene bunod, and an intermediate therefor.

BACKGROUND ART

Latanoprostene bunod of the following formula (1) (4-(nitrooxy)butyl (Z)-7-((1R,2R,3R,5S)-3,5-dihydroxy-2-((R)-3-hydroxy-5-phenylpentyl)cyclopentyl)hept-5-enoate) is an active pharmaceutical ingredient (API) of Vesneo® which is a medicine for glaucoma.

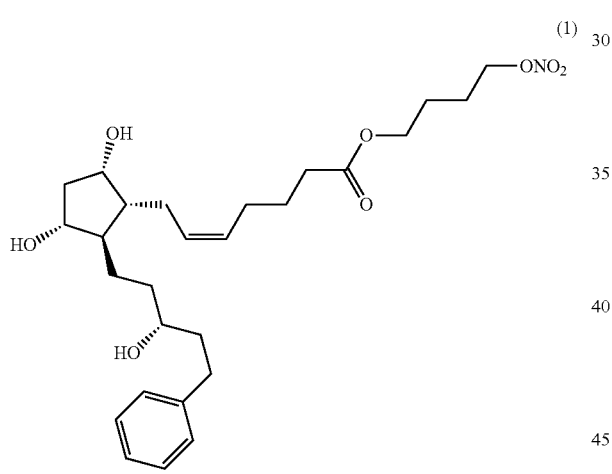

(1)

U.S. Pat. No. 7,273,946 discloses a process for preparing latanoprostene bunod by preparing 4-bromobutyl nitrate using tetrahydrofuran as a starting material and subjecting it to combination reaction with latanoprost acid, as shown in the following reaction scheme 1. However, the preparation process has the danger of using strong acids in the synthesis of 4-bromobutyl nitrate, and the risk of explosion due to rapid heat generation in dropwise addition of sulfuric acid into nitric acid solution. Further, the bromide produced by the combination reaction reacts with the nitrate of latanoprostene bunod, which causes the problem of producing a large amount of by-products.

[Reaction Scheme 1]

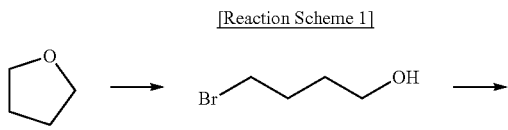

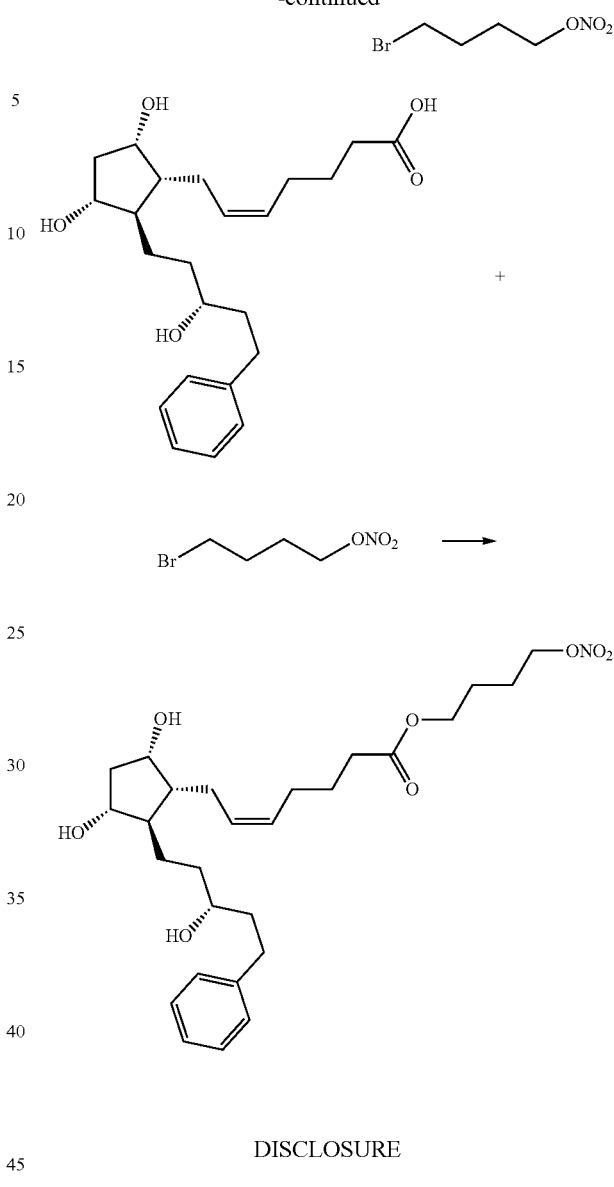

DISCLOSURE

Technical Problem

It is an object of the present invention to provide an efficient and cost-effective process for preparing latanoprostene bunod.

It is another object of the present invention to provide an intermediate for the above preparation process.

Technical Solution

One embodiment of the present invention relates to a process for preparing latanoprostene bunod of the following formula (1), which comprises the steps of:

(i) subjecting a compound of the following formula (3) to esterification with a compound of the following formula (4) to obtain a compound of the following formula (5); and (ii) subjecting the bromide of the compound of the following formula (5) to nitration:

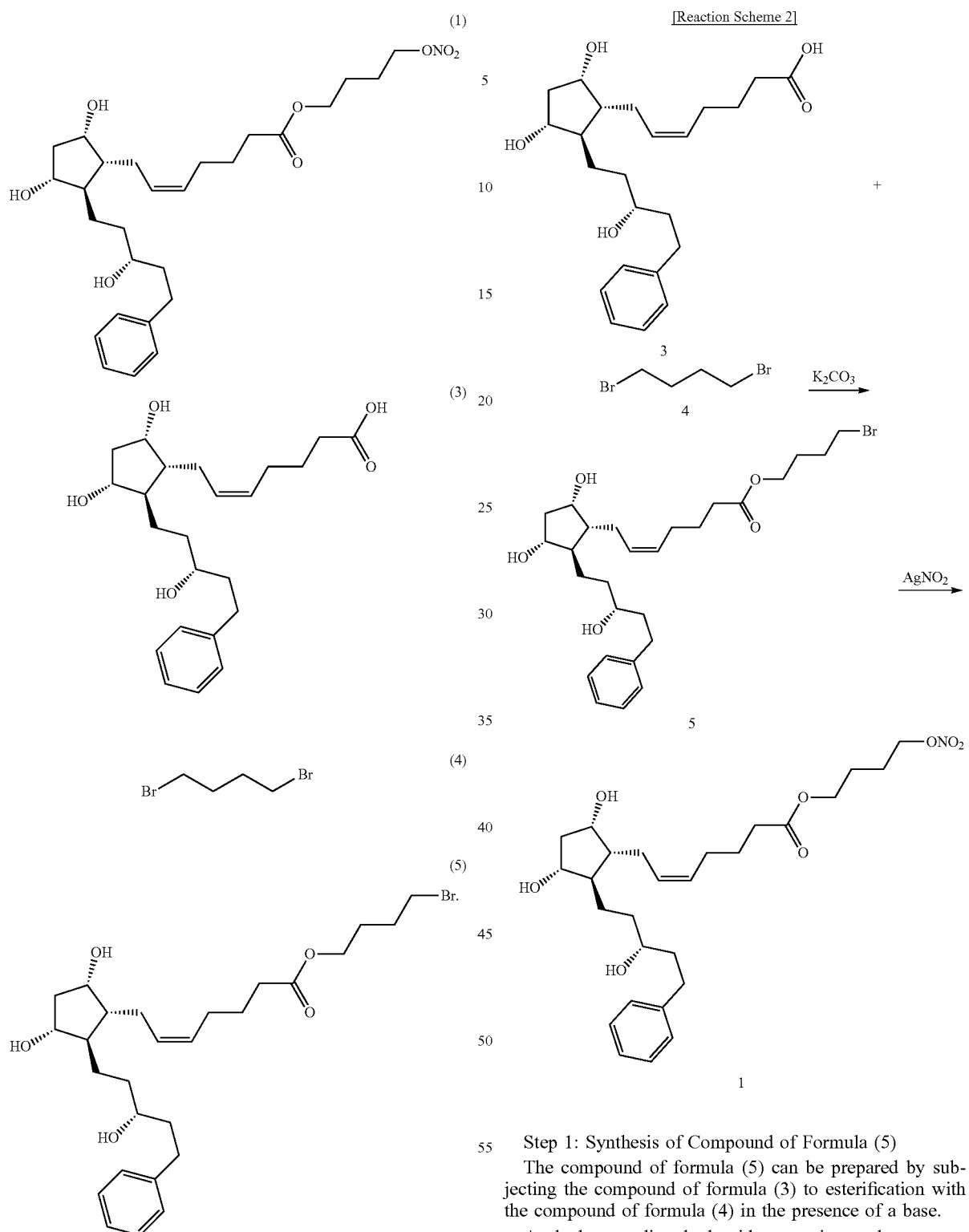

Hereinafter, the preparation process of the present invention is described in more detail referring to the following reaction scheme 2. The process depicted in the following reaction scheme 2 represents merely a typical example, and various changes may be made to reagents and reaction conditions without limitation.

Step 1: Synthesis of Compound of Formula (5)

The compound of formula (5) can be prepared by subjecting the compound of formula (3) to esterification with the compound of formula (4) in the presence of a base.

As the base, sodium hydroxide, potassium carbonate, etc. may be used.

Particularly, potassium carbonate is preferred.

As the reaction solvent, toluene, tetrahydrofuran, dimethylformimide, etc. may be used. Particularly, dimethylformimide is preferred.

The reaction temperature is suitably about 40 to 50° C., and the reaction time is preferably about 2 hours.

Step 2: Preparation of Compound of Formula (1)

The compound of formula (1) can be prepared by subjecting the bromide of the compound of formula (5) to nitration.

The nitration may be carried out by substitution reaction using a nitrate. As the nitrate, silver nitrate ($AgNO_3$) is preferred. When the silver nitrate is used, silver bromide (AgBr) formed in the substitution reaction is precipitated, thereby reducing side reactions.

As the reaction solvent, acetonitrile is preferred.

The reaction temperature is suitably about 30 to 40° C., and the reaction time is preferably about 40 to 50 hours.

In one embodiment of the present invention, the compound of formula (3) may be prepared by hydrolyzing an isopropyl ester group of a compound of the following formula (2).

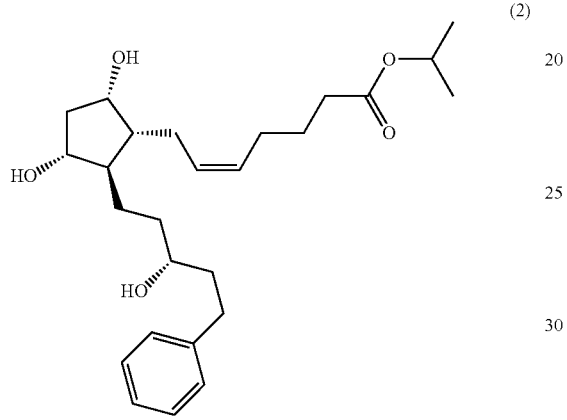

(2)

The hydrolysis may be carried out using sodium hydroxide, potassium hydroxide, lithium hydroxide monohydrate, etc. Particularly, lithium hydroxide monohydrate is preferred.

As the reaction solvent, ethanol, methanol, water, or a mixture thereof may be used. Particularly, a mixture of methanol and water is preferred.

The reaction temperature is suitably room temperature, and the reaction time is preferably 15 to 20 hours.

One embodiment of the present invention relates to a compound of the following formula (5) which is an intermediate for the preparation of latanoprostene bunod.

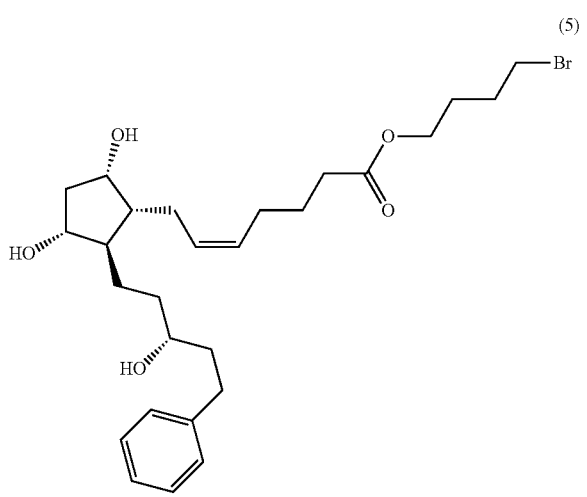 [SMILES: O=C(CCC/C=C\C[C@@H]1[C@@H](CC[C@@H](O)CCc2ccccc2)[C@H](O)C[C@@H]1O)OCCCCBr]

(5)

One embodiment of the present invention relates to a process for preparing the compound of formula (5), which comprises a step of:

(i) subjecting a compound of the following formula (3) to esterification with a compound of the following formula (4):

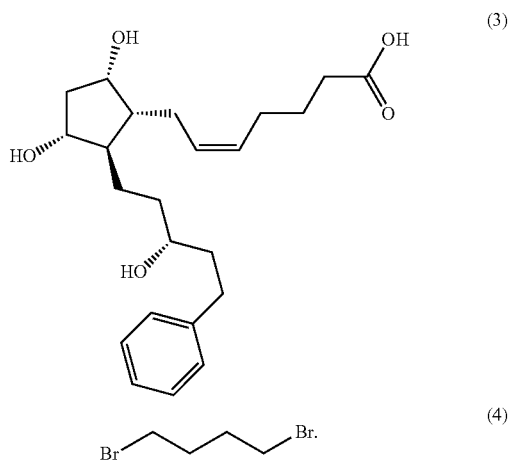

The process for preparing the compound of formula (5) includes the same step (i) as in the above process for preparing latanoprostene bunod, and thus a detailed description thereof will be omitted.

Advantageous Effects

In accordance with the preparation process of the present invention, latanoprostene bunod of formula (1) can be efficiently and cost-effectively prepared while reducing side reactions.

BEST MODE

The present invention will be described in more detail by following examples. It will be obvious to those skilled in the art that these examples are merely described for illustration of the present invention and the scope of the present invention is not limited thereto.

Preparation Example 1: Preparation of Compound of Formula (3)

Latanoprost (2) (30 g) was dissolved in methanol (600 mL), and water (120 mL) and lithium hydroxide monohydrate (14.55 g) were added thereto, followed by stirring at room temperature for about 15 hours. The process of the reaction was observed by thin layer chromatography (ethyl acetate:methanol=15:1). After the completion of the reaction, the reaction solvent was concentrated, and 1M ammonium chloride (300 mL), 2M sodium hydrogen sulfate (300 mL) and ethyl acetate (300 mL) were added thereto, followed by stirring for about 15 to 20 minutes. The organic layer was separated, and dried over anhydrous sodium sulfate, followed by filtration, and concentration under reduced pressure. The resulting residue was purified by chromatography using a silica gel (ethyl acetate:methanol=5:1) to give pure latanoprost acid ((Z)-7-((1R,2R,3R,5S)-3,5-dihydroxy-2-((R)-3-hydroxy-5-phenylpentyl)cyclopentyl)hept-3-enoic acid) (3) (23.9 g, 88%).

¹H NMR (300 MHz, CDCl₃): 7.30-7.25 (2H, m), 7.20-7.14 (3H, m), 5.53-5.30 (2H, m), 4.16-4.08 (5H, m), 3.95-3.94 (1H, m), 3.74-3.66 (1H, m), 2.84-2.60 (2H, m), 2.36-2.31 (2H, t, J=6.7 Hz), 2.27-2.23 (2H, t, J=7.2 Hz), 2.18-2.10 (2H, q, J=7.3 Hz), 1.88-1.86 (2H, m), 1.84-1.47 (8H, m), 1.40-1.32 (2H, m);

¹³C NMR (300 MHz, CDCl₃): δ=177.5, 142.2, 129.6, 129.5, 128.6, 126.0, 78.7, 74.6, 71.7, 52.6, 51.9, 42.6, 38.9, 35.3, 33.2, 32.2, 29.2, 26.8, 26.5, 24.8, 14.3.

Example 1: Preparation of Compound of Formula (5)

The compound of formula (3) (22.8 g) was dissolved in dimethylformimide (342 mL), and potassium carbonate (24.2 g) and 1,4-dibromobutane (4) (37.8 g) were added thereto, followed by heating and stirring at about 40 to 50° C. for about 2 hours. The process of the reaction was observed by thin layer chromatography (ethyl acetate 100%). After the completion of the reaction, saturated sodium chloride aqueous solution (684 mL) and ethyl acetate (684 mL) were added thereto, followed by stirring for about 15 to 20 minutes. The organic layer was separated and washed with saturated sodium chloride aqueous solution (456 mL). The organic layer was separated and dried over anhydrous sodium sulfate, followed by filtration, and concentration under reduced pressure. The resulting residue was purified by chromatography using a silica gel (ethyl acetate 100%) to give pure 4-bromobutyl (Z)-7-((1R,2R,3R,5S)-3,5-dihydroxy-2-((R)-3-hydroxy-5-phenylpentyl)cyclopentyl)hept-3-enoate (5) (25.5 g, 83%).

¹H NMR (300 MHz, CDCl₃): 7.31-7.16 (5H, m), 5.51-5.35 (2H, m), 4.17 (1H, s), 4.12-4.08 (2H, t, J=6.3 Hz), 3.95 (1H, s), 3.69-3.65 (1H, m), 3.45-3.41 (2H, t, J=6.5 Hz), 2.85-2.63 (2H, m), 2.60 (1H, s), 2.38-2.30 (3H, m), 2.28-2.07 (3H, m), 1.98-1.59 (14H, m), 1.56-1.47 (1H, m), 1.44-1.25 (2H, m);

¹³C NMR (300 MHz, CDCl₃): δ=174.0, 142.2, 129.6, 129.5, 128.6, 128.5, 126.0, 79.0, 74.9, 71.4, 69.6, 53.1, 52.0, 42.7, 39.2, 35.9, 33.8, 33.2, 32.3, 29.8, 29.4, 27.4, 27.1, 26.8, 25.0.

Example 2: Preparation of Compound of Formula (1)

The compound of formula (5) (25.5 g) was dissolved in acetonitrile (382 mL), and silver nitrate (16.5 g) was added thereto, followed by heating and stirring at about 30 to 40° C. for about 40 to 50 hours. The process of the reaction was observed by thin layer chromatography (hexane:ethanol=5:1). After the completion of the reaction, the reaction product was cooled to room temperature, and the insoluble solid was removed by a celite filtration. The filtrate was concentrated under reduced pressure, and ethyl acetate (382 mL) and water (382 mL) were added thereto, followed by stirring for about 15 to 20 minutes. The organic layer was separated, and saturated sodium chloride aqueous solution (382 mL) was added thereto, followed by stirring for about 10 to 15 minutes. The organic layer was separated and dried over anhydrous sodium sulfate, followed by filtration, and concentration under reduced pressure. The resulting residue was purified by chromatography using a silica gel (hexane:ethanol=5:1) to give pure 4-(nitrooxy)butyl (Z)-7-((1R,2R,3R,5S)-3,5-dihydroxy-2-((R)-3-hydroxy-5-phenylpentyl)cyclopentyl)hept-3-enoate (1) (14.0 g, 56.8%).

¹H NMR (300 MHz, CDCl₃): 7.31-7.26 (2H, m), 7.21-7.15 (3H, m), 5.51-5.34 (2H, m), 4.49-4.45 (2H, t, J=6.2 Hz), 4.16-4.15 (1H, m), 4.12-4.08 (2H, t, J=6.0 Hz), 3.95-3.94 (1H, m), 3.67 (1H, m), 2.85-2.75 (1H, m), 2.72-2.62 (2H, m), 2.40-2.38 (1H, d, J=5.8 Hz), 2.35-2.30 (2H, t, J=7.3 Hz), 2.28-2.21 (1H, m), 2.17-2.09 (2H, m), 1.87-1.86 (2H, m), 1.84-1.58 (12H, m), 1.56-1.47 (1H, m), 1.43-1.27 (2H, m);

¹³C NMR (300 MHz, CDCl₃): δ=173.9, 142.2, 129.6, 129.5, 128.5, 128.5, 125.9, 78.9, 74.9, 72.7, 71.4, 63.6, 53.0, 52.0, 42.6, 39.2, 35.9, 33.9, 32.2, 29.7, 27.1, 26.7, 25.1, 24.9, 23.8.

The invention claimed is:

1. A process for preparing latanoprostene bunod of the following formula (1), which comprises the steps of:
   (i) subjecting a compound of the following formula (3) to esterification with a compound of the following formula (4) to obtain a compound of the following formula (5); and
   (ii) subjecting the bromide of the compound of the following formula (5) to nitration:

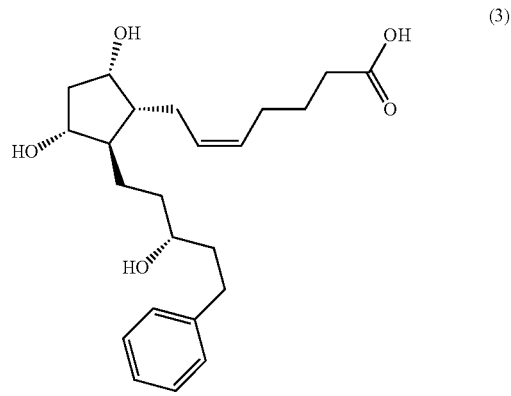

(3)

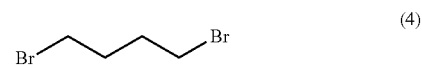

(4)

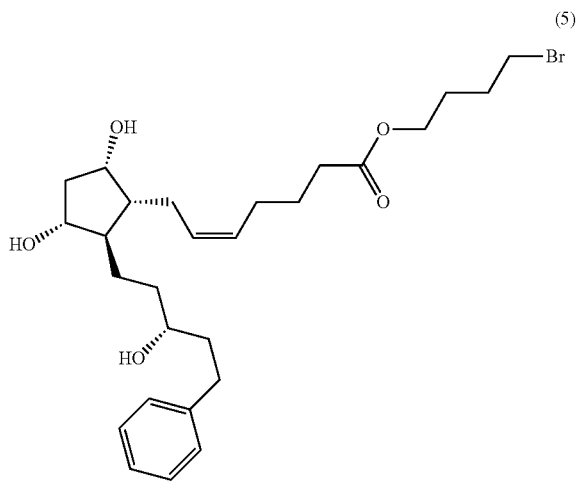 [SMILES: O=C(CCC/C=C\C[C@@H]1[C@@H](CC[C@@H](O)CCc2ccccc2)[C@H](O)C[C@@H]1O)OCCCCBr]

(5)

-continued

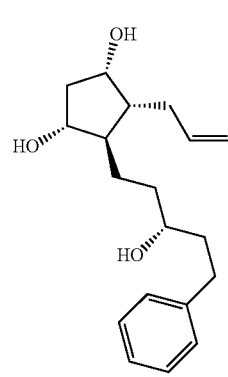

(1)

2. The process according to claim 1, wherein the esterification of step (i) is carried out in the presence of a base.

3. The process according to claim 2, wherein the base is potassium carbonate.

4. The process according to claim 1, wherein the nitration of step (ii) is carried out using silver nitrate (AgNO₃).

5. The process according to claim 1, wherein the compound of formula (3) is prepared by hydrolyzing an isopropyl ester group of a compound of the following formula (2):

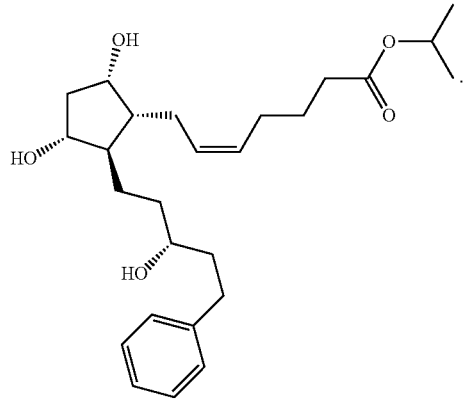

(2)

6. The process according to claim 5, wherein the hydrolysis is carried out using lithium hydroxide monohydrate.

7. A compound of the following formula (5):

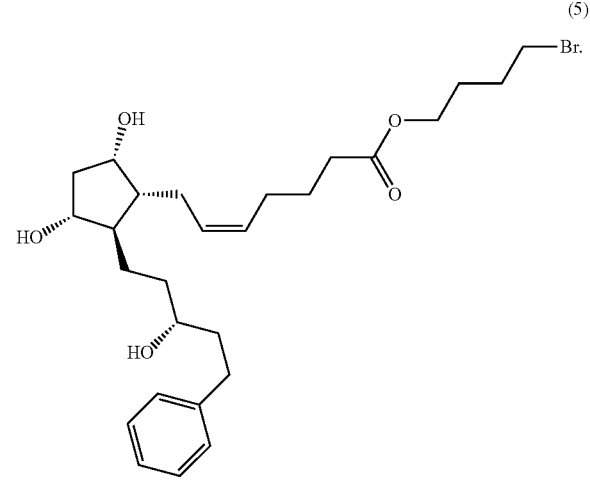

(5)

8. A process for preparing a compound of the following formula (5), which comprises a step of:
(i) subjecting a compound of the following formula (3) to esterification with a compound of the following formula (4):

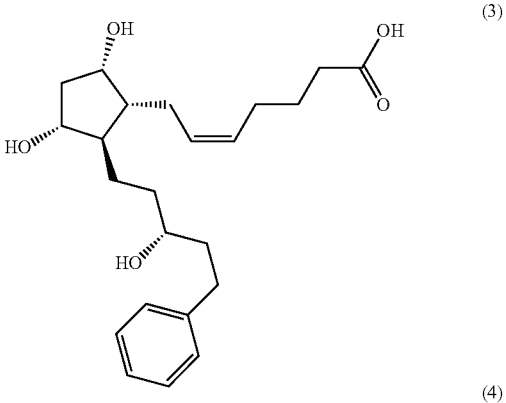

(3)

(4)

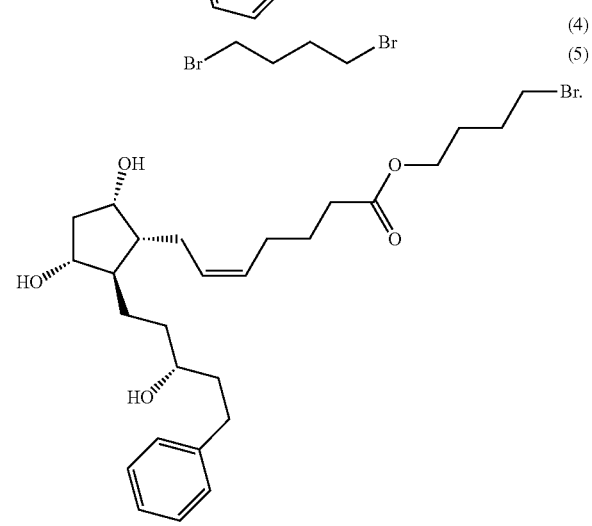

(5)

* * * * *